United States Patent [19]

Horodysky et al.

[11] 4,152,275

[45] May 1, 1979

[54] SULFURIZED OLEFIN ADDUCTS OF PHOSPHORODITHIOIC ACIDS AND ORGANIC COMPOSITIONS CONTAINING SAME

[75] Inventors: Andrew G. Horodysky, Cherry Hill; Milton Braid, Westmont, both of N.J.

[73] Assignee: Mobil Oil Corporation, New York, N.Y.

[21] Appl. No.: 864,052

[22] Filed: Dec. 23, 1977

[51] Int. Cl.$^2$ .............................................. C10M 1/48
[52] U.S. Cl. ............................ 252/46.6; 252/400 A; 260/125; 260/139; 260/934; 260/965; 260/978
[58] Field of Search .................... 252/46.6, 400 A; 260/125, 139, 934, 965, 978

[56] References Cited

U.S. PATENT DOCUMENTS

| | | | |
|---|---|---|---|
| 3,013,971 | 12/1961 | Mastin | 252/46.6 X |
| 3,536,812 | 10/1970 | Oswald et al. | 252/46.6 X |
| 3,558,490 | 1/1971 | Lowe | 252/46.6 |
| 3,770,854 | 11/1973 | Morris et al. | 252/46.6 X |
| 3,880,735 | 4/1975 | Oswald | 252/46.6 X |
| 3,929,653 | 12/1975 | Elliott et al. | 252/46.6 X |

*Primary Examiner*—Delbert E. Gantz
*Assistant Examiner*—Andrew Metz
*Attorney, Agent, or Firm*—Charles A. Huggett; Raymond W. Barclay; Howard M. Flournoy

[57] ABSTRACT

A novel product formed by the reaction of dialkyl or diaryl phosphorodithioic acid and a sulfurized olefin possesses good copper corrosivity, good antiwear and antioxidant activity. Organic compositions containing a minor amount thereof also possess good lubricating characteristics.

36 Claims, No Drawings

SULFURIZED OLEFIN ADDUCTS OF PHOSPHORODITHIOIC ACIDS AND ORGANIC COMPOSITIONS CONTAINING SAME

BACKGROUND OF THE INVENTION

1. Field of the Invention

This invention is directed to novel compounds comprising adducts of alkyl or aryl phosphorodithioic acids and a sulfurized olefin.

2. Summary of the Prior Art

Sulfurized olefins are known to be effective extreme pressure agents or load carrying additives for lubricating oils; U.S. Pat. Nos. 3,703,504; 3,697,499 and 3,471,404.

Phosphorodithioic acids have been reacted with olefins; see for example, U.S. Pat. Nos. 3,646,172 and 3,350,348, and A. A. Oswald, Journal Organic Chemistry, 27, 2439 (1962). However, none of these processes are similar to the instant process nor are the compounds so produced similar to the novel adducts of this invention.

It has now been discovered that when a dialkyl or diaryl phosphorodithioic acid is added in low concentration to the unsaturated components of certain sulfurized olefins low phosphorus (0.1–10%), high sulfur (ca. 25% or more) content products result. These products have improved oil solubility and odor as compared to the sulfurized olefin and impart good antiwear and antioxidant activity, and good copper corrosivity to organic substrates, e.g., lubricating oils, when incorporated therein.

SUMMARY OF THE INVENTION

This invention is directed to organothiophosphorus compounds comprising the reaction product of a phorosphorodithioic acid having the general formula

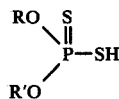

wherein R and R' are hydrocarbyl and are the same or different with each having up to about 30 carbon atoms. Thus, R and R' may each be alkyl of 1 to about 30 carbon atoms, aryl and alkaryl or aralkyl of 7 to about 30 carbon atoms. Accordingly, when alkyl R and R' are selected from a group consisting of, for example, $CH_3$, $C_2H_5$, n—$C_3H_7$, i—$C_3H_7$, n—$C_4H_9$, i—$C_4H_9$, n—$C_5H_{11}$, i—$C_5H_{11}$, $C_5H_{11}$, $C_6H_{13}$, n—$C_5H_{11}(C_2H_5)CH_2$ and mixtures thereof, i.e. R and R' may be methyl, ethyl, n-propyl, isopropyl, n-butyl, isobutyl, pentyl or amyl, hexyl, ethylhexyl, oleyl, etc. and mixtures thereof; and a sulfurized olefin containing reactive olefinic sites wherein said sulfurized olefin is derived from a process comprising sulfohalogenating a hydrocarbon olefin having a single double bond and having from 2 to about 8 carbon atoms per molecule with a sulfur halide selected from the group consisting of sulfur chlorides and sulfur bromides to form a sulfohalogenated intermediate and thereafter sulfurizing and dehalogenating said intermediate by treatment with an aqueous alkali metal monosulfide solution such as described in U.S. Pat. No. 3,703,504. The alkali metal monosulfide solution may comprise sodium, potassium, or lithium sulfide and may contain sodium hydroxide, sodium hydrosulfide, sodium cresylates, sodium sulfate, sodium chloride, oil and ferrous sulfide.

This invention is also directed to organic compositions comprising a major amount of an organic medium normally subject to deterioration and a minor amount of an additive sufficient to impart antiwear and antioxidant characteristics thereto comprising an organothiophosphorus compound in accordance with this invention and wherein said organic medium is a lubricant composition consisting of oils of lubricant viscosity selected from the group comprising hydrocracked oils, automotive oils, gear oils, transmission fluids, hydraulic oils, waxes and greases prepared from said oils of lubricating viscosity which may be mineral oils or fractions thereof, synthetic oils or mixtures of synthetic and mineral oils.

DESCRIPTION OF SPECIFIC EMBODIMENTS

The phosphorodithioic acids in accordance with this invention are generally prepared from the reaction of a suitable phosphorus sulfide, e.g., phosphorus pentasulfide with a variety of phenolic or alcoholic materials preferably a hydroxylic compound ROH where R may be aryl or alkyl of up to about 30 carbon atoms. A nonexhaustive list of suitable hydroxylic compounds include phenol, methanol, ethanol, n-propanol, i-propanol, n-butanol, i-butanol, primary and secondary pentanols, hexanol, ethylhexanol, oleyl alcohol and/or mixtures thereof.

The preparation of the phosphorodithioic acids may be carried out in any convenient manner known to the art. These acids may also be obtained commercially or made, for example, by slowly reacting a mixture of phosphorus sulfide and the aforementioned hydroxylic component.

Sulfurized olefins useful herein are generally described in U.S. Pat. No. 3,703,504 the entirety of which is incorporated herein by reference. This class of reactant, however, is not limited thereto.

Generally speaking, the sulfurized olefins are obtained via a process which comprises sulfohalogenating an olefin with a sulfur halide in the presence of a catalytic quantity (i.e., 0.2–10 wt. % based on the halide) of a lower aliphatic alcohol (such as methanol, ethanol, propanol, i-propanol, butanol, i-butanol, i.e., having up to about 10 carbon atoms) to form a sulfohalogenated organic intermediate, and thereafter sulfurizing and dehalogenating said intermediate in the presence of a substantial quantity of lower aliphatic alcohol, e.g., from 10 to about 50% by weight of the adduct by treatment with an aqueous alkali metal sulfide solution, or an aqueous alkali metal monosulfide solution (which can be derived, for example, from a spent aqueous alkali metal hydroxide effluent from hydrocarbon purification) having a substantial combined sulfur content thus producing an organic sulfide of high combined sulfur content.

A wide variety of olefinic substances may be charged to the initial sulfochlorination reaction including olefins having a single double bond as terminal or internal double bonds. The olefinic substances usually contain from about 2 to 8 or more carbon atoms per molecule in either straight, branched chain or cyclic compounds. These may be exemplified by ethylene, propylene, butene-1, cis- and trans- butene-2, isobutylene, diisobutylene, triisobutylene, the pentenes, cyclopentene, the hexenes, cyclohexene, the octenes and decene-1. Isobutylene is the preferred olefinic reactant. In general, $C_{3-6}$ olefins or mixtures thereof are desirable for preparing sulfurized products for use herein as lube oil additives; the combined sulfur content of the product decreases with increasing carbon content while its miscibility with oil is lower for propylene and ethylene derivatives.

The other reactant in the first stage is preferably sulfur monochloride ($S_2Cl_2$); but other similar compounds such as sulfur dichloride and $S_3Cl_2$ as well as the corresponding sulfur bromides may be employed in an amount which will provide a quantity of sulfur corresponding to desirable reactant ratios for sulfur monochloride. The molar ratio of olefin to sulfur monohalide may range from about 1:1 up to 1.7:1 or more. In the case of isobutylene and sulfur monochloride, the optimum ratio appears to be between about 1.55:1 and 1.60:1.

The initial reaction can be catalyzed with a lower aliphatic alcohol containing from 1 to 4 carbon atoms, as exemplified by methanol, ethanol, propanol and isopropanol. Of these, methanol and ethanol are usually preferred. The spent aqueous alkali metal hydroxide effluent as mentioned hereinabove is derived primarily from spent organic caustic liquors issuing from integrated refinery processes.

After mixing the spent caustic solutions, the approximate composition of such a mixture from a typical refinery may be exemplified as:

|  | Weight percent |
| --- | --- |
| Sodium hydroxide | 6.1 – 6.3 |
| Sodium hydrosulfide | 4.9 – 5.4 |
| Sodium cresylates[1] | 14.6 – 20.4 |
| Sodium sulfate | 0.5 – 0.7 |
| Sodium chloride | 0.04 – 0.06 |
| Oil | 0.3 – 0.4 |
| Ferrous sulfide-(5–10 ppm) |  |
| Water | ca. 66.7 – 73.6 |

[1]Sodium salts of cresols, thiocresols, phenol, thiophenol and the xylenols.

The sulfurized olefins produced by the above-described process have a very high sulfur content of more than about 35% by weight (typically about 46–48% combined sulfur and are substantially devoid of free sulfur). Other sulfurized olefins made by variations of this process or by other processes known to the art which contain reactive olefinic sites and have a sulfur content of about 30% and above may also be employed in this invention. The novel compounds of this invention may thus be prepared by adding phosphorodithioic acids in low concentrations to such sulfurized olefins. These compounds have a low phosphorus content from 0.1 to 5–10 weight percent, and a high sulfur content of about 25–35% or more. The low phosphorus content inter alia may account for improved oil solubility, improved odor and improved copper strip corrosivity.

The reaction is usually carried out at temperatures of from about 75° to 120° C., preferably from 80°–110° C., under atmospheric pressure (although higher pressures may be used if desired) for periods of up to about 16–20 hours, e.g., preferably from about 1 to about 10 hours or more. The reaction mixture is heated with agitation to the desired temperature. The reaction may be accelerated by sparging catalytic amounts of hydrogen sulfide to the reaction vessel to increase the product yield. The reaction may also be carried out in the absence of any added solvent or it may be carried out in a non-reactive solvent such as pentane, hexane, heptane, cyclohexane, benzene, toluene and the like or a refined petroleum oil may be employed therefor.

The novel compounds comprising an adduct of dialkyl or diaryl phosphorodithioic acid as heretofore described with sulfurized olefins such as those disclosed in accordance with U.S. Pat. No. 3,703,504 may be used effectively as antiwear/antioxidant additives and copper corrosion inhibitors. Any effective amount of the additive compound may be used varying up to about 10% by weight or more. Preferably the organic medium or substrate, e.g., oil of lubricating viscosity contains from about 0.01 to 5% and more preferably from about 0.05 to about 2.5% by weight of the total weight of the lubricant composition. As hereinbefore indicated, the organic sulfur and phosphorus-containing complexes may be incorporated into any lubricating media which can include oils of lubricating viscosity and also greases in which any of the aforementioned oils are employed as vehicles. In general, synthetic oils can also be effectively protected against the above-noted deterioration or degradation. They may also be employed in combination with mineral oils, and ester base stock, or as grease vehicles. Typical synthetic vehicles include polyisobutylene, polybutenes, hydrogenated polydecenes, polypropylene glycol, polyethylene glycol, trimethlolpropane esters, neopentyl alcohol and pentaerythritol esters, di(2-ethylhexyl) sebacate, di(2-ethylhexyl) adipate, dibutyl phthalate, fluorocarbons, esters of phosphorus-containing acids, liquid ureas, ferrocene derivatives, hydrogenated mineral oils, chain-type polyphenols, siloxanes and silicones (polysiloxanes), alkyl-substituted diphenyl ethers typified by a butyl-substituted bis-(p-phenoxyphenyl) ether and phenoxyphenyl ether.

EXAMPLE 1

Preparation of Sulfurized Olefin

Sulfurized olefin was prepared in accordance with Example 1 of U.S. Pat. No. 3,703,504 using isobutylene. The yield of sulfurized organic product amounted to 98% of theory, had a sulfur content of 47% by weight and a chlorine content of only 0.11% as well as a clear, light orange brown color, and a high flash point of 250° F.

EXAMPLE 2

Preparation of Sulfurized Olefin

Sulfurized olefin was prepared in general accordance with Example 6 of U.S. Pat. No. 3,703,504. A mixture of sulfurized organic compounds using mixed butylene reactants obtained from a petroleum refinery stream instead of the isobutylene was obtained using the same reaction conditions and molar ratios of reactants. Ignoring the small water content, the predominantly olefinic mixture employed in this instance had the following composition by volume:

| Component | Volume percent |
| --- | --- |
| Propylene | 0.2 |
| Propane | 1.0 |
| Isobutane | 3.4 |
| Butane | 10.5 |
| Isobutylene | 48.2 |
| Butene-1 | 31.5 |
| Trans-2-butane | 4.1 |
| Cis-2-butene | 0.2 |
| Butadiene | 0.4 |
| Methylacetylene | 0.1 |
| Other hydrocarbons | 0.4 |
|  | 100.0 |

The product obtained by reacting the tabulated hydrocarbon mixture was more complex than that obtained with the isobutylene reactant; however, its properties resemble those of the product of Example 1 as evidenced by the following characteristics:

| Sulfur content | 46.8% |
|---|---|
| Chlorine content | 0.13% |
| Viscosity | 12.3 cs/210° F. |

EXAMPLE 3

Preparation of Sulfurized Olefin

Sulfurized olefin was prepared in general accordance with Example 6 of U.S. Pat. No. 3,703,504. A mixture of butylene was sulfurized using the same reaction conditions described and an equivalent molar ratio of flake sodium monosulfide ($Na_2S$). The olefin mixture employed in this instance had the following composition by volume:

| Component | Volume percent |
|---|---|
| Isobutylene | 90.5 |
| Trans-2-butane | 5.9 |
| Cis-2-butene | 2.6 |
| Butadiene | 1.0 |
| | 100.0 |

The product had the following characteristics:

| Sulfur content | 45.87% |
|---|---|
| Chlorine content | 0.27% |
| Viscosity | 12.1 cs/210° F. |

EXAMPLE 4

Adduct of O,O-Diisobutylphosphorodithioic Acid

O,O-Diisobutylphosphorodithioic acid was made by the reaction of $P_2S_5$ with isobutanol following the general procedure previously described. Approximately 535 grams of isobutanol were reacted with 395 grams of $P_2S_5$ at about 70° to 80° F. for about 4 hours. The by-product $H_2S$ was vented. The solution was cooled and filtered to remove unreacted $P_2S_5$. Approximately 750 grams of the aforementioned sulfurized olefin prepared in accordance with Example 1 was reacted with 150 grams of O,O-diisobutylphosphorodithioic acid at 90°–100° C. for about 10 hours with a slow $H_2S$ sparge to form an adduct. The crude reaction product was washed with dilute aqueous caustic to remove any unreacted phosphorodithioic acid; no unreacted acid was recovered from the caustic washed. After water washing and drying a clear yellow liquid was recovered in 97% yield, based on reactants charged.

Product analysis:

| | Found | Calculated |
|---|---|---|
| Phosphorus, Wt. % | 1.60 | 2.1 |
| Sulfur, Wt. % | 40.6 | 41.8 |
| Carbon, Wt. % | 45.6 | — |
| Hydrogen, Wt. % | 7.10 | — |

EXAMPLE 5

Adduct of O,O-Diisobutylphosphorodithioic Acid

Another sample of sulfurized olefin (740 grams) as prepared in Example 1 was reacted with O,O-diisobutylphosphorodithioic acid (520 grams) at 85°–90° C. for about 8 hours to form an adduct. After washing, a clear yellow liquid was isolated containing 2.81% phosphorus, 38.3% sulfur, 47.4% carbon and 7.98% hydrogen.

EXAMPLE 6

Adducts of Mixed O-2-Propyl-O-2-ethylhexylphosphorodithioic Acid

High and low phosphorus content adducts of mixed O-2-propyl-O-2-ethylhexylphosphorodithioic acid were prepared.

A. O-2-propyl-O-2-ethylhexylphosphorothioic acid was made following the procedure of Example 4 by the reaction of an equal molar mixture of 2-propanol and 2-ethylhexanol with phosphorus pentasulfide. Approximately 180 grams of the sulfurized olefin prepared in accordance with Example 1 was then reacted with 213 grams (0.84 mole) of the phosphorodithioic acid to form a high phosphorus content adduct. After washing and drying the product was isolated as a clear yellow liquid of high phosphorus content.

B. A low phosphorus content adduct was prepared by reacting 800 grams of sulfurized olefin as prepared in accordance with Example 1 with 250 grams of O-2-propyl-O-2-ethylhexylphosphorodithioic acid and slowly bubbling in small amounts of hydrogen sulfide. After a ten hour reaction period, it was found that 95% of the phosphorodithioic acid had reacted with the sulfurized olefin. The crude reaction product was washed with dilute aqueous caustic, water and then dried and filtered. Yellow clear liquid product was obtained.

| | High P | Low P |
|---|---|---|
| Phosphorus, Wt. % | 3.88 | 1.97 |
| Sulfur, Wt. % | 32.0 | 37.7 |
| Carbon, Wt. % | 51.4 | 45.9 |
| Hydrogen, Wt. % | 7.95 | 7.08 |

EXAMPLE 7

Adduct of O,O-Diphenylphosphorodithioic Acid

Approximately 200 grams of sulfurized olefin as prepared in accordance with Example 1 was reacted with 35 grams of O,O-diphenylphosphorodithioic acid for 9 hours at 100°–105° C. with a slow introduction of hydrogen sulfide. Almost all of the O,O-diphenylphosphorodithioic acid was found to react with the sulfurized olefin; no unreacted phosphorodithioic acid was readily isolated. The product comprised the sulfurized olefin adduct with O,O-diphenylphosphorodithioic acid.

| Phosphorus, Wt. % | 1.13 |
|---|---|
| Sulfur, Wt. % | 40.9 |
| Carbon, Wt. % | 43.6 |
| Hydrogen, Wt. % | 6.34 |

EXAMPLE 8

Adduct of O,O-Di-n-butylphosphorodithioic Acid

O,O-di-n-butylphosphorodithioic acid was made by reaction of $P_2S_5$ with n-butanol. Approximately 245 grams of sulfurized olefin (Example 1) was reacted with 143 grams (0.6 mole) of the phosphorodithioic acid by heating with agitation to a temperature of from 75°–95° C. After washing with dilute aqueous caustic to remove approximately 40 grams of unreacted phosphorodithioic acid, the resulting clear yellow liquid was composed of approximately 30% wt. of the phosphorodithioic acid moiety (a). The preparation was repeated several times varying the quantities of reagents (b) is a median result; and including an aqueous sodium sulfide wash in the presence of isopropanol.

|  | (a) Adduct | (b) Repeat Adduct | Adduct-Isopropanol (c)Na$_2$S Wash | (d) |
|---|---|---|---|---|
| Phosphorous, Wt. % | 4.04 | 4.32 | 3.65 | 2.80 |
| Sulfur, Wt. % | 38.0 | 35.0 | 35.1 | 35.8 |
| Carbon, Wt. % | 43.9 | 45.6 | 46.3 | 49.4 |
| Hydrogen, Wt. % | 7.58 | 7.49 | 7.34 | 7.46 |

EXAMPLE 9

Adduct of O,O-Dioleylphosphorodithioic Acid

O,O-Dioleylphosphorodithioic acid was reacted with sulfurized olefin as prepared in accordance with Example 1. Approximately 120 grams of O,O-dioleylphosphorodithioic acid was reacted with 380 grams of sulfurized olefin at about 100° C. for 7 hours with a slow hydrogen sulfide sparge. The crude reaction product was washed with dilute aqueous ammonium hydroxide and dried.

| Phosphorus, Wt. % | 1.10 |
|---|---|
| Sulfur, Wt. % | 36.0 |
| Carbon, Wt. % | 48.3 |
| Hydrogen, Wt. % | 7.68 |

EXAMPLE 10

Adduct of Mixed O-2-Propyl O-2-ethylhexylphosphorodithioic Acid

Approximately 16 grams of O-2-propyl O-2-ethylhexylphosphorodithioic acid was reacted with 34 grams of sulfurized olefin prepared in accordance with Example 2. After an eight hour reaction period at 295° C. with a slow hydrogen sulfide sparge, the crude product was washed with dilute aqueous caustic water washed and dried. A clear yellow liquid was isolated.

| Phosphorus, Wt. % | 2.97 |
|---|---|
| Carbon, Wt. % | 47.93 |
| Hydrogen, Wt. % | 8.02 |

EXAMPLE 11

Adduct of Mixed O-2-Propyl O-2-ethylhexylphosphorodithioic Acid

Approximately 18½ grams of O-2-propyl O-2-ethylhexylphosphorodithioic acid was reacted with 32½ grams of sulfurized olefin prepared in accordance with Example 3. After a 5½ hour reaction period at about 95° C. with a slow hydrogen sulfide sparge, the crude product was washed with dilute aqueous caustic, water washed and dried. A pale yellow clear liquid was obtained.

| Phosphorus, Wt. % | 3.07 |
|---|---|
| Sulfur, Wt. % | 34.5 |
| Hydrogen, Wt. % | 7.39 |

Representative samples of the thus prepared adducts were thereafter tested for their antiwear effectiveness in accordance with the standard 4-Ball Wear Test.

TABLE 1

4 Ball Wear Scar Diameter (MM)
½" Balls, 52100 Steel, 60 KG Load, 30 Minutes

| Additive | Conc. Wt. % | Temp., °F. | Speed (RPM) | | | |
|---|---|---|---|---|---|---|
| | | | 500 | 1000 | 1500 | 2000 |
| Base Stock* | 100 | Room | 0.50 | 0.60 | 0.88 | 2.34 |
| | | 200 | 0.60 | 1.06 | 1.86 | 2.23 |
| | | 390 | 1.00 | 1.31 | 2.06 | — |
| Adduct of O,O-Diisobutyl-phosphorodithioic Acid (Example 5) | 1.0 | Room | 0.40 | 0.60 | 0.70 | 1.15 |
| | | 200 | 0.70 | 0.80 | 0.80 | 1.5 |
| | | 390 | 0.60 | 0.90 | 1.85 | 1.85 |
| Adduct of Mixed O-2-Propyl O-2-ethylhexylphosphoro-dithioic Acid (Example 6a) | 1.0 | Room | 0.40 | 0.75 | 0.80 | 0.90 |
| | | 200 | 0.90 | 1.00 | 0.90 | 1.30 |
| | | 390 | 0.80 | 1.10 | 1.50 | 1.50 |
| Adduct of O,O-Diphenylphosphorodithioic Acid (Example 7) | 1.0 | Room | 0.50 | 0.70 | 0.80 | 1.25 |
| | | 200 | 0.50 | 0.60 | 0.90 | 1.15 |
| | | 390 | 2.00 | 1.55 | 1.66 | 1.70 |
| Adduct of O,O-Di-n-butyl-phosphorodithioic Acid (2.8% P) (Example 8d)[1] | 1.0 | Room | 0.40 | 0.60 | 0.80 | 0.90 |
| | | 200 | 0.95 | 0.70 | 0.80 | 1.20 |
| | | 390 | 0.09 | 1.55 | 1.50 | |
| Adduct of O,O-Di-n-butyl-phosphorodithioic (4.3% P) (Example 8b) | 1.0 | Room | 0.80 | 1.00 | 0.75 | 1.15 |
| | | 200 | 1.05 | 0.80 | 0.90 | 1.25 |
| Adduct of O,O-Di-n-butyl phosphorodithioic Acid sulfurized with Na$_2$S (3.65% P) (Example 8c)[1] | 1.0 | Room | 0.50 | 0.80 | 0.75 | 1.25 |
| | | 200 | 0.90 | 0.90 | 0.80 | 2.00 |
| | | 390 | 0.85 | 1.70 | 1.5 | 2.00 |
| Adduct of O,O-Dioleylphosphorodithioic Acid | 1.0 | Room | 0.40 | 0.70 | 0.70 | 1.40 |
| | | 200 | 0.55 | 1.00 | 0.90 | 1.20 |

TABLE 1-continued

4 Ball Wear Scar Diameter (MM)
¼" Balls, 52100 Steel, 60 KG Load, 30 Minutes

| Additive | Conc. Wt. % | Temp., °F. | Speed (RPM) | | | |
|---|---|---|---|---|---|---|
| | | | 500 | 1000 | 1500 | 2000 |
| (2.7% P) (Example 9) | | 390 | 1.00 | 0.80 | 1.70 | 1.55 |

*The base stock was an 80/20 mixture of bright stock mineral oil and 200" solvent paraffinic neutral lubricating oils.
¹Example having in addition an aqueous sulfide wash in presence of isopropanol.

Representative samples of the above prepared adducts were also tested (Table 2) for copper corrosivity ASTM No. D130-9 at 210° F. for 6 hours and also for antioxidant properties (Table 3) with a catalytic oxidation test at 325° C. for 40 hours as described below.

TABLE 2
Cu Corrosion (210° F., 6 hours) ASTM No. D130-9

Base Oil — an 80/20 mixture of bright stock mineral oil and 200" solvent paraffinic neutral mineral oil except for Example 5 which is entirely 200" solvent paraffinic neutral mineral oil.

| Example No. | 1% |
|---|---|
| Example 3 | 3A |
| Example 4 | 2B |
| Example 5 | 3A |
| Example 6A | 2B |
| Example 6B | 2B |
| Example 8 | |
| (a) | 3A |
| (b) | 2B |
| (c) Adduct with isopropanol | 1B |
| (d) Na₂S wash | 1B |
| Example 9 | 1B |
| Example 10 | 1B |
| Example 11 | 2B |

The lower the rating the better the additive performance.

Catalytic Oxidation Test

A sample of the base lubricant is placed in an oven at a desired temperature. Present in the sample are the following metals either known to catalyze organic oxidation or commonly used materials of construction.

a. 15.6 sq. in. of sand-blasted iron wire,
 b. 0.78 sq. in. of polished copper wire,
 c. 0.87 sq. in. of polished aluminum wire, and
 d. 0.167 sq. in. of polished lead surface.

Dry air is passed through the sample at a rate of about 5 liters per hour.

TABLE 3

| | Catalytic Oxidation Test (325° F., 40 hours) | | | |
|---|---|---|---|---|
| Example No. | Pb loss mg. | Percent increase in viscosity of oxidized oil, KV at 210° F. | Neutralization Number (NN) | Sludge |
| Base Stock, 0% Additive (200" solvent paraffinic neutral) | 0.4 | 27 | 2.21 | Heavy |
| Example 4, 1% | 0.0 | 3 | 0.72 | Heavy |
| 3% | 0.0 | 5 | 0.74 | Heavy |
| Example 5, 1% | 0.5 | 1 | 0.94 | Trace |
| 3% | 0.4 | 0 | 1.16 | Light |
| Example 6a, 1% | 0.2 | 9.4 | 1.99 | Moderate |
| Example 6b, 1% | 0.0 | 3 | 0.66 | Heavy |
| 3% | 0.0 | 4.4 | 0.73 | Heavy |
| Example 7, 1% | 0.3 | 5 | 0.76 | Moderate |
| 3% | 0.5 | 5 | 0.74 | Moderate |
| Example 8a, 1% | 0.5 | 10 | 1.77 | Light |
| b, 1% | 0.5 | 9 | 1.72 | Light |
| c, 1% | 0.0 | 22 | 1.60 | Heavy |
| d, 1% | 0.1 | 7 | 0.58 | Moderate |
| Example 9, 1% | 0.2 | 7 | 0.86 | Light |
| Example 10, 1% | 0.3 | 6 | 1.64 | Heavy |
| Example 11, 1% | 0.2 | 4 | 1.43 | Moderate |

The data shown in the tables clearly establish that the novel compounds of this invention provide good antioxidant and antiwear properties to lubricants while maintaining or improving good copper strip corrosivity.

While the process of the present invention has been described in detail in conjunction with the treatment of a limited number of compounds under similar conditions for the purposes of valid comparisons and of fully illustrating the invention, it will be readily apparent to those of ordinary skill in the art that numerous modifications and variations are within the purview of this invention.

What is claimed is:

1. An organothiophosphorus compound comprising the reaction product of a phosphorodithioic acid having the general formula:

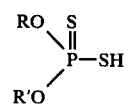

wherein R and R' are hydrocarbyl, R and R' may be the same or different with each having up to about 30 carbon atoms, and a sulfurized olefin having from about 2 to 8 carbon atoms and having at least about 25–35 wt. % of combined sulfur and sufficient reactive olefinic sites to react with said acid whereby the resultant organothiophosphorous compound has from about 0.1 to 5–10 wt. % of phosphorous.

2. The product of claim 1 wherein the sulfurized olefin is derived from a process comprising sulfohalogenating a hydrocarbon olefin having a single double bond and from 3 to about 6 carbon atoms per molecule with a sulfur halide selected from the group consisting of sulfur chlorides and sulfur bromides in the presence of a catalytic quantity of a lower aliphatic alcohol to form a sulfohalogenated intermediate and thereafter sulfurizing and dehalogenating said intermediate in the presence of a substantial quantity of a lower aliphatic alcohol by treatment with an aqueous alkali metal sulfide solution.

3. The product of claim 2 wherein said sulfohalogenated intermediate is treated with an aqueous alkali metal sulfide solution, said sulfide solution being a monosulfide solution comprising sodium hydroxide, sodium hydrosulfide, sodium cresylates, sodium sulfate, sodium chloride, oil and ferrous sulfide.

4. The compound described in claim 1 wherein R and R' are selected from the group consisting of $C_1$–$C_{30}$ alkyl, aryl and $C_7$–$C_{30}$ alkaryl or aralkyl.

5. The compound of claim 1 wherein R and R' are each alkyl of 1 to about 30 carbon atoms.

6. The compound of claim 5 wherein R and R' are both n-butyl.

7. The compound of claim 5 wherein R and R' are both isobutyl.

8. The compound of claim 5 wherein R and R' are both oleyl.

9. The compound of claim 5 wherein R is propyl and R' is ethylhexyl.

10. The compound of claim 1 wherein R and R' are each aryl.

11. The compound of claim 10 wherein R and R' are each phenyl.

12. The compound of claim 1 wherein the olefin sulfurized comprises isobutylene.

13. The compound of claim 1 wherein the sulfurized olefin comprises a major portion of mixed isomeric butenes.

14. A process according to claim 2 wherein the phosphorodithioic acid and the sulfurized olefin are reacted in a weight ratio of olefin to acid of from about 0.15:1 to about 10:1 at temperature of from about 25 to 150° C. for a period of from 1 to about 20 hours under atmospheric pressure.

15. A process according to claim 14 wherein the sulfurized olefin is derived in the presence of a lower alcohol selected from methanol, ethanol, propanol, i-propanol, butanol and i-butanol and mixtures thereof.

16. A process according to claim 15 in which methanol is present in the sulfohalogenation reaction and i-propanol is present in said sulfurizing reaction wherein said sulfohalogenated intermediate is formed.

17. A process according to claim 16 in which said methanol amounts to between about 0.2 and 10% of the weight of said sulfur halide and said isopropanol amounts to at least about 25% of the weight of said intermediate.

18. A process according to claim 1 in which said olefin contains from 3 to 6 carbon atoms per molecule, and the final organic sulfide product has a content of combined sulfur in excess of about 35% by weight.

19. A process according to claim 1 in which said olefin comprises at least a major proportion of isobutylene, and the final organic sulfide product has a content of combined sulfur in excess of 35% by weight.

20. A process according to claim 15 in which said sulfur halide is sulfur monochloride.

21. A process according to claim 20 in which the molar ratio of said olefin to said sulfur monochloride is between about 1:1 and 1.7:1.

22. A process according to claim 20 in which the molar ratio of said olefin to said sulfur monochloride is between about 1.55:1 and 1.60:1.

23. A composition comprising a major amount of an organic medium wherein said organic medium is an oil of lubricating viscosity which is normally subject to deterioration and a minor amount of an additive sufficient to impart antiwear, antioxidant and copper corrosivity characteristics thereto of an organothiophosphorus compound in accordance with claim 1.

24. The composition of claim 23 wherein R and R' of said organothiophosphorus compounds are each alkyl of 1 to about 30 carbon atoms.

25. The composition of claim 24 wherein R and R' are each selected from the group consisting of methyl, ethyl, n-propyl, isopropyl, n-butyl, isobutyl, pentyl, hexyl, ethylhexyl, oleyl and mixtures thereof.

26. The composition of claim 25 wherein R and R' are both n-butyl.

27. The composition of claim 25 wherein R and R' are both isobutyl.

28. The composition of claim 25 wherein R and R' are both oleyl.

29. The composition of claim 25 wherein R is propyl and R' is ethylhexyl.

30. The composition of claim 23 wherein R and R' are each aryl.

31. The composition of claim 30 wherein R and R' are each phenyl.

32. The composition of claim 23 wherein the oil of lubricating viscosity is selected from the group consisting of hydrocracked oils, automotive oils, gear oils, transmission fluids, hydraulic oils waxes, and greases prepared from said oils of lubricating viscosity which may be mineral oils or fractions thereof, synthetic oils or mixtures of synthetic and mineral oils.

33. The composition of claim 32 wherein the oil of lubricating viscosity is a mineral oil.

34. The composition of claim 32 wherein the oil of lubricating viscosity is a synthetic oil.

35. The composition of claim 34 wherein the synthetic oil has an ester base.

36. The composition of claim 32 wherein the lubricant composition is a grease.

* * * * *